US009079848B2

(12) United States Patent
Miyake et al.

(10) Patent No.: US 9,079,848 B2
(45) Date of Patent: Jul. 14, 2015

(54) 5-ACETOXY-(E3)-3-PENTENYL METHOXYMETHYL ETHER AND METHOD FOR PREPARING (E3)-3-ALKENYL ACETATE USING THE SAME

(71) Applicant: Shin-Etsu Chemical Co., Ltd., Tokyo (JP)

(72) Inventors: Yuki Miyake, Joetsu (JP); Naoki Ishibashi, Joetsu (JP); Miyoshi Yamashita, Joetsu (JP); Takehiko Fukumoto, Joetsu (JP)

(73) Assignee: Shin-Etsu Chemical Co., Ltd., Tokyo (JP)

( * ) Notice: Subject to any disclaimer, the term of this patent is extended or adjusted under 35 U.S.C. 154(b) by 0 days.

(21) Appl. No.: 13/790,940

(22) Filed: Mar. 8, 2013

(65) Prior Publication Data

US 2013/0245313 A1    Sep. 19, 2013

(30) Foreign Application Priority Data

Mar. 13, 2012 (JP) ................................. 2012-055855

(51) Int. Cl.
*C07C 69/145* (2006.01)
*C07C 41/48* (2006.01)
*C07C 29/128* (2006.01)
*C07C 67/08* (2006.01)

(52) U.S. Cl.
CPC ............... *C07C 67/08* (2013.01); *C07C 29/128* (2013.01); *C07C 41/48* (2013.01); *C07C 69/145* (2013.01)

(58) Field of Classification Search
CPC ...... C07C 67/08; C07C 69/145; C07C 41/48; C07C 29/128
USPC ................................................ 560/261, 262
See application file for complete search history.

(56) References Cited

U.S. PATENT DOCUMENTS 5,728,376 A * 3/1998 Attygalle et al. ............... 424/84

FOREIGN PATENT DOCUMENTS

JP      2009-132647 A    6/2009
WO     WO 96/33612 A1   10/1996

OTHER PUBLICATIONS

Backvall, et al., "Regiocontrol in Copper-Catalyzed Grignard Reactions with Allylic Substrates," J. Am. Chem. Soc., 112, 6615-6621.*
Yamakawa et al., "(5R, 7R)-5-Methylheptadecan-7-ol: a novel sex pheromone component produced by a femal lichen moth, *Miltochrista calamina*, n the family Artiidae," Tetrahedron Letters, 52, 5808-5811, 2011.*
CAS Registry, CAS No. 805239-82-1 and CAS No. 177408-54-7.*

Coldham, et al., "Intramolecular carbolithiation reactions for the preparation of 3-alkenylpyrrolidines," Org. Biomol. Chem., 2003, 1, 2111-2119.*
Shibata et al., "Syntheses of Racemic and Diastereomeric Mixtures of 3,7,11,15-Tetramethylhentriacontane and 4,8,12,16-Tetramethyldotriacontane, the Cuticular Tetramethylalkanes of the Tsetse Fly, Glossina brevippalpis," Biosci., Biotechnol. Biochem., 66(3) 582-587, 2002.*
Attygalle, A. B., et al.; "*(3E, 8Z 11Z)-3,8,11-Tetradecatrienyl Acetate, Major Sex Pheromone Component of Tomato Pest Scrobipalpuloides absoluta (Lepidoptera: Gelechiidae);*" Bioorganic & Medicinal Chemisty, Vo. 4, No. 3; pp. 305-314; dated 1996.
Attygalle, A. B., et al.; "*Microscale Random Reduction: Application to the Characterization of (3E, 8Z, 11Z)-3,8,11-Tetradecatrienyl Acetate, a New Lepidopteran Sex Pheromone;*" Tetrahedron Letters, vol. 36, No. 31; pp. 5471-5474; dated 1995.
Hungerford, N. L., et al.; "*Titanium(II)-based Z-reduction of alkynes. Syntheses of deuterium labeled linolenic and oleic acids and (3E, 8Z, 11Z)-tetradeca-3,8,11-trienyl acetate, the sex pheromone of a tomato pest, Scrobipalpuloides absoluta;*" Journal of the Chemical Society, Perkin Transactions 1, No. 11; pp. 183-1858; dated 1998.
Svatos, A., et al.; "*Sex Pheromone of Tomato Pest Scrobipalpuloides absoluta (Lepidoptera: Gelechiidae);*" Journal of Chemical Ecology, vol. 22, No. 4; pp. 787-800; dated 1996.
European Search Report for Application No. EP 13 15 8915 dated Jun. 20, 2013.
Attygalle, A. B. et al., *Microscale, Random Reduction: Application to the Characterization of (3E,8Z,11Z)-3,8,11-Tetradecatrienyl Acetate, a New Lepidopteran Sex Pheromone*, Terrahedron Letters, vol. 36, No. 31 (1995) 5471-5474.
Bartels, B. et al., *Asymmetric Ir¹-Catalysed Allylic Alkylation of Monosubstituted Allylic Acetates With Phosphorus Amidites As Ligands*, Eur. J. Org. Chem. (2002) 1097-1103.
Bartels, B. et al., *Iridium-Catalysed Allylic Substitution: Stereochemical Aspects and Isolation of Ir$^{III}$ Complexes Related to the Catalytic Cycle*, Eur. J. Inorg. Chem. (2002) 2569-2586.
Hungerford, N. L. et al., *Titanium (II)-based Z-reduction of Alkynes: Stereo-and Regio-specific Z-dideuteriation of Conjugated and Methylene-skipped ynes*, Chem. Commun. (1996) 1697-1698.
Office Action from Japanese Patent Application No. 2012-055855, dated Jul. 4, 2014.

(Continued)

*Primary Examiner* — Paul A Zucker
*Assistant Examiner* — Mark Luderer
(74) *Attorney, Agent, or Firm* — Alston & Bird LLP

(57) ABSTRACT

Provided are 5-acetoxy-(E3)-3-pentenyl methoxymethyl ether which can be prepared in conventional reaction equipment and a method for preparing an (E3)-3-alkenyl acetate by using it. More specifically, 5-hydroxy-(E3)-3-pentenyl methoxymethyl ether obtained by reacting 4-formyl-(E3)-3-butenyl methoxymethyl ether with a reductant is reacted with an acetylating agent to prepare 5-acetoxy-(E3)-3-pentenyl methoxymethyl ether. (E3)-3-alkenyl methoxymethyl ether obtained by a coupling reaction between the 5-acetoxy-(E3)-3-pentenyl methoxymethyl ether and a Grignard reagent is treated with an acid, and then reacted with an acetylating agent to prepare the (E3)-3-alkenyl acetate.

1 Claim, No Drawings

(56) References Cited

OTHER PUBLICATIONS

Office Action for Chinese Application No. 201310075675.8 dated Jan. 14, 2015.
Carey, F. A. et al., *Advanced Organic Chemistry* (vol. B Reaction and Synthesis), Advanced Education Press (Jan. 1986) 101-102.
Li, J. J. et al., *Modern Organic Synthesis in the Laboratory*, Oxford University Press, Inc. (2007) 88-89.
Office Action from Japanese Patent Application No. 2012-055855, dated Sep. 11, 2014.
Shin Kagaku Jikken Kouza (New Chemical Experiment Course) No. 15 "Sanka to Kange (Oxidation and Reduction) II", (1977) 179-207.

\* cited by examiner

5-ACETOXY-(E3)-3-PENTENYL METHOXYMETHYL ETHER AND METHOD FOR PREPARING (E3)-3-ALKENYL ACETATE USING THE SAME

BACKGROUND OF THE INVENTION

1. Field of the Invention

The present invention relates to 5-acetoxy-(E3)-3-pentenyl methoxymethyl ether and a method for preparing (E3)-3-alkenyl acetate using the same. The (E3)-3-alkenyl acetate includes, for example, (E3,Z8,Z11)-3,8,11-tetradecatrienyl acetate and (E3,Z8)-3,8-tetradecadienyl acetate which are sex pheromone substances of tomato pest *Tuta absoluta*.

2. Description of the Related Art

*Tuta absoluta* is a serious tomato pest. The larvae thrive inside tomato leaves, tomato fruits and the like which are not easily exposed to a chemical liquid. Accordingly, it is difficult to control them by using insecticides. In addition, because there is almost no natural enemy found in Europe recently attacked by the pest, the increased damage thereby cannot be stopped. Therefore, biological control methods are attracting attentions and use of a sex pheromone substance is expected as one of these methods.

As a main component of the sex pheromone composition of *Tuta absoluta*, (E3,Z8,Z11)-3,8,11-tetradecatrienyl acetate was identified (Attygalle et al. Bioorg. Med. Chem. 1996, 4(3): 305 to 314). Subsequently, (E3,Z8)-3,8-tetradecadienyl acetate was found as the second component and it was shown that a 10:1 weight ratio mixture of them had higher attraction effect than the main component alone (Svatoš et al. J. Chem. Ecol. 1996, 22(4): 787-800).

Several new methods for synthesizing the sex pheromone substance are reported. For example, it is reported (J. N. Jham et al. Tetrahedron Lett. 1995, 36(31), 5471-5474) that the substance can be obtained by hydroaluminating (Z8,Z11)-8,11-tetradecadienyl-3-yl-1-ol with lithium aluminum hydride, followed by acetylation. It is also reported (A. L. Hungerf et al. J. Chem. Soc., Perk in Transl, 1998, 1839) that the substance can be obtained by subjecting tetrahydropyranyl-protected (Z8,Z11)-8,11-tetradecadienyl-3-yl-1-ol to Birch reduction to remove the tetrahydropyranyl group, followed by acetylation.

SUMMARY OF THE INVENTION

The preparation method of J. N. Jham et al. (Tetrahedron Lett. 1995, 36(31), 5471-5474) uses ignitable lithium aluminum hydride so that the method has a problem for industrial scale preparation. The preparation method of A. L. Hungerf et al. (J. Chem. Soc., Perk in Transl, 1998, 1839) uses ammonia, which is a deleterious and offensive odor substance, during Birch reduction so that it has a problem in equipment from the standpoint of ammonia treatment.

With the foregoing in view, the invention has been made. An object of the invention is to provide 5-acetoxy-(E3)-3-pentenyl methoxymethyl ether which can be prepared using conventional reaction equipment and a method for preparing (E3)-3-alkenyl acetate using it.

The present inventor have found that (E3)-3-alkenyl acetate can be obtained in a good yield without deteriorating the purity of the double bond at the 3-position by synthesizing 5-acetoxy-(E3)-3-pentenyl methoxymethyl ether obtainable in a large amount at a low cost and having a very high E-isomer purity, and then subjecting the 5-acetoxy-(E3)-3-pentenyl methoxymethyl ether to a coupling reaction with a Grignard reagent, and have completed the invention.

According to the invention, there is provided 5-acetoxy-(E3)-3-pentenyl methoxymethyl ether. There is also provided a method for preparing 5-acetoxy-(E3)-3-pentenyl methoxymethyl ether comprising at least the steps of reacting 4-formyl-(E3)-3-butenyl methoxymethyl ether with a reductant to obtain 5-hydroxy-(E3)-3-pentenyl methoxymethyl ether, and reacting the 5-hydroxy-(E3)-3-pentenyl methoxymethyl ether with an acetylating agent. There is further provided a method for preparing (E3)-3-alkenyl acetate, comprising at least the steps of subjecting the 5-acetoxy-(E3)-3-pentenyl methoxymethyl ether to a coupling reaction with a Grignard reagent represented by the following formula:

RMgX wherein R represents a linear, branched or cyclic $C_{1-20}$ hydrocarbon group which may have optional one or more double bonds and X represents a halogen atom, so that the 5-acetoxy group is replaced by R to obtain (E3)-3-alkenyl methoxymethyl ether; treating the (E3)-3-alkenyl methoxymethyl ether with an acid to obtain (E3)-3-alkenyl alcohol; and reacting the (E3)-3-alkenyl alcohol with an acetylating agent to obtain (E3)-3-alkenyl acetate.

According to the invention, 5-acetoxy-(E3)-3-pentenyl methoxymethyl ether having a very high E-isomer purity can be obtained highly reliably in a large amount at a low cost without using an ignitable reagent and without using special equipment.

Moreover, according to the invention, a high-purity (E3)-3-alkenyl acetate can be prepared efficiently by subjecting the 5-acetoxy-(E3)-3-pentenyl methoxymethyl ether to a coupling reaction with a Grignard reagent.

DETAILED DESCRIPTION OF THE INVENTION

5-Acetoxy-(E3)-3-pentenyl methoxymethyl ether is prepared, for example, by reducing 4-formyl-(E3)-3-butenyl methoxymethyl ether (1) and then acetylating the reduced compound. At this time, since the protecting group for the alcohol is a methoxymethyl group, the reaction proceeds under any of basic and acidic conditions with the protecting group un-removed and 5-acetoxy-(E3)-3-pentenyl methoxymethyl ether can be obtained in a good yield. The reaction in the subsequent step also proceed in a good yield owing to the presence of this protecting group so that an (E3)-3-alkenyl acetate can be synthesized in a high yield.

The starting substance, 4-formyl-(E3)-3-butenyl methoxymethyl ether (1), can be prepared, for example, by protecting the hydroxyl group of 3-butyn-1-ol with a methoxymethyl group, converting the hydrogen of the terminal alkyne to an acetal, hydrogenating the alkyne, and then hydrolyzing the acetal. In order to hydrogenate the carbon triple bond into a carbon double bond, a known catalyst can be used. For example, a Lindlar catalyst can be used.

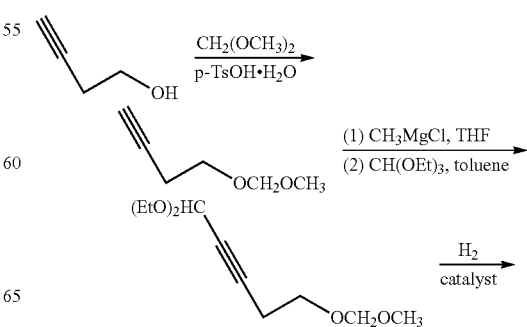

-continued

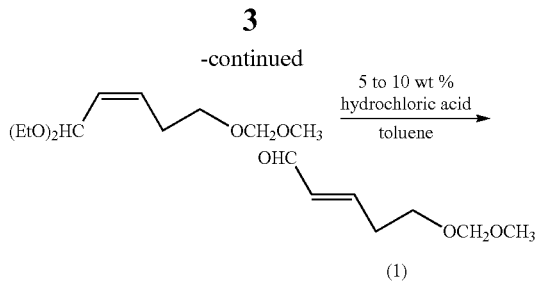

wherein p-TsOH.H$_2$O represents para-toluenesulfonic acid monohydrate, THF represents tetrahydrofuran, and Et represents an ethyl group.

The 4-formyl-(E3)-3-butenyl methoxymethyl ether (1) is reacted with a reductant to prepare 5-hydroxy-(E3)-3-pentenyl methoxymethyl ether (2). Examples of the reductant include diisobutylaluminum hydride, lithium aluminum hydride, sodium borohydride and lithium borohydride. Sodium borohydride is preferred from the standpoint of reactivity.

This reduction reaction can be conducted, for example, by adding dropwise a sodium hydroxide solution of sodium borohydride to the 4-formyl-(E3)-3-butenyl methoxymethyl ether in a solvent.

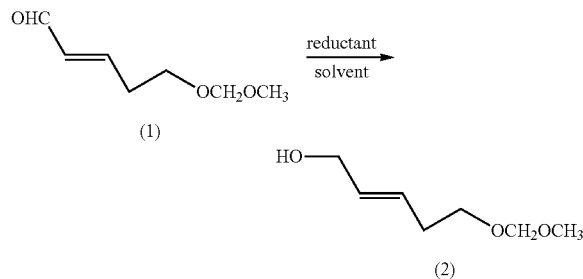

The reductant is added in an amount of preferably from 0.3 to 1.5 mol per mol of 4-formyl-(E3)-3-butenyl methoxymethyl ether (1). When diisobutylaluminum hydride is used as the reductant, its amount is preferably from 1.0 to 1.5 mol. The amount of less than 1.0 mol may be insufficient to complete the reaction. The amount of more than 1.5 mol may lead to wasting of the reductant. When the other reductant is used, its amount is preferably from 0.3 to 1.0 mol. The amount of less than 0.3 mol may be insufficient to complete the reaction. The amount of more than 1.0 mol may lead to wasting of the reductant.

Examples of the solvent to be used for the reduction reaction include various alcohols such as methanol and ethanol, hydrocarbons such as toluene and hexane, and ethers such as tetrahydrofuran and diethyl ether. Toluene is preferred from the standpoint of reaction efficiency. In this reaction, the solvent can be used in an amount of preferably from 50 to 300 g per mol of the 4-formyl-(E3)-3-butenyl methoxymethyl ether (1). The amount of less than 50 g may retard the reaction, while the amount of more than 300 g may lead to wasting of the solvent and reduction in the charged amount of reactants.

The reaction temperature to be used in the reduction reaction is preferably from 0 to 20° C. The temperature of less than 0° C. may retard the reaction, while that of more than 20° C. may cause a side reaction such as an aldol reaction.

5Hydroxy-(E3)-3-pentenyl methoxymethyl ether (2) can be reacted with an acetylating agent to prepare 5-acetoxy-(E3)-3-pentenyl methoxymethyl ether (3). Examples of the acetylating agent include acetyl chloride; condensation agents such as dicyclohexylcarbodiimide; and acetic anhydride. Acetic anhydride is preferred from the standpoint of reactivity.

This acetylation reaction can be conducted, for example, by reacting 5-hydroxy-(E3)-3-pentenyl methoxymethyl ether (2) with acetic anhydride in a solvent in the presence of a pyridine compound or an amine compound.

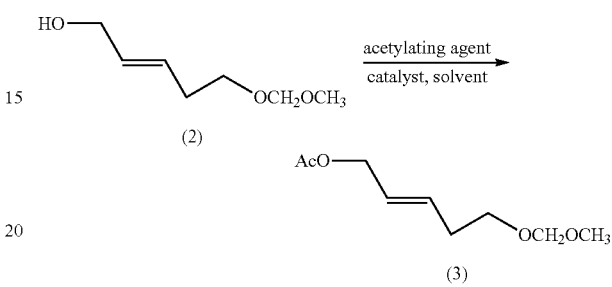

wherein Ac represents an acetyl group.

The acetylating agent can be used in an amount of preferably from 1.1 to 1.3 mol per mol of 5-hydroxy-(E3)-3-pentenyl methoxymethyl ether (2). The amount of less than 1.1 mol may prevent the smooth progress of the reaction, while the amount of more than 1.3 mol may lead to wasting of the agent.

The acetylation reaction can proceed in a solvent-free manner, but it may be conducted in a solvent.

Examples of the catalyst to be used for the acetylation reaction may include pyridine compounds such as pyridine and dimethylaminopyridine, and amine compounds such as triethylamine and trimethylamine. Dimethylaminopyridine is preferred from the standpoint of catalytic activity. The catalyst is used in an amount of preferably from 0.002 to 0.01 mol per mol of 5-hydroxy-(E3)-3-pentenyl methoxymethyl ether (2).

Examples of the solvent to be used for the acetylation reaction include hydrocarbons such as toluene and hexane, and ethers such as tetrahydrofuran and diethyl ether. Toluene is preferred from the standpoint of reactivity. The above reaction may proceed in a solvent-free manner, but when the solvent is used, it is used in an amount of preferably 200 g or less per mol of 5-hydroxy-(E3)-3-pentenyl methoxymethyl ether (2). The amount of more than 200 g may lead to wasting of the solvent and reduction in the charged amount of reactants.

The reaction temperature to be used for the acetylation reaction is preferably from 6 to 90° C., more preferably from 6 to 70° C. The temperature of less than 6° C. may retard the reaction, while the temperature of more than 90° C. may have the methoxymethyl ether protecting group removed.

Next, a method for preparing (E3)-3-alkenyl acetate (6) by using the 5-acetoxy-(E3)-3-pentenyl methoxymethyl ether (3) will be explained.

A coupling reaction between 5-acetoxy-(E3)-3-pentenyl methoxymethyl ether (3) and a Grignard reagent produces (E3)-3-alkenyl methoxymethyl ether (4) having R in the place of the 5-acetoxy group. The methoxymethyl group is stable under a basic condition so that the deprotected alcohol cannot be obtained by the coupling reaction. The yield of this reaction is as high as about 90%. In addition, no E-Z isomerization is found during the reaction.

The coupling reaction is conducted, for example, between 5-acetoxy-(E3)-3-pentenyl methoxymethyl ether (3) and a Grignard reagent represented by the following formula:
RMgX
wherein R represents a linear, branched or cyclic hydrocarbon group which has from 1 to 20 carbon atoms, preferably from 1 to 15 carbon atoms and may have optional one or more double bonds and X represents a halogen atom,
in a solvent in the presence of a catalyst, preferably in the presence of a catalyst and an auxiliary catalyst.

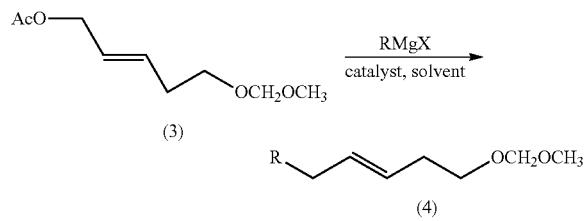

wherein Ac represents an acetyl group.

Examples of R having no double bond include a linear hydrocarbon group such as hexyl, decyl and tetradecyl; a branched hydrocarbon group such as isopropyl, tert-butyl and 2-ethylhexyl; and a cyclic hydrocarbon group such as cyclopropyl and cyclooctyl. Examples of R having one or more double bonds include a hydrocarbon group having from 1 to 4 double bonds such as nonenyl, nonadienyl, undecatrienyl and dodecatetraenyl.

X represents a halogen atom such as chlorine, bromine or iodine. Chlorine is preferred from the standpoint of reactivity.

The Grignard reagent can be used in an amount of preferably from 1.0 to 1.5 mol, more preferably from 1.1 to 1.2 mol per mol of 5-acetoxy-(E3)-3-pentenyl methoxymethyl ether (3). The amount of less than 1.0 mol may not let the reaction proceed smoothly, while the amount of more than 1.5 mol may lead to wasting of the reagent.

When (Z3,Z6)-3,6-nonadienylmagnesium halide in which R is a nonadienyl group, which is a linear diene hydrocarbon group having 9 carbon atoms, is used as the Grignard reagent, (E3,Z8,Z11)-3,8,11-tetradecatrienyl methoxymethyl ether can be produced. Using this product as an intermediate, (E3,Z8,Z11)-3,8,11-tetradecatrienyl acetate, a main component of the sex pheromone composition of Tuta absoluta, can be synthesized.

Similarly, when (Z3)-3-nonenylmagnesium halide in which R is a nonenyl group, which is a linear monoene hydrocarbon group having 9 carbon atoms, is used as the Grignard reagent, (E3,Z8)-3,8-tetradecadienyl methoxymethyl ether can be produced. Using this product as an intermediate, (E3,Z8)-3,8-tetradecadienyl acetate, a second component of the sex pheromone composition of *Tuta absoluta*, can be synthesized.

Examples of the catalyst to be used for the coupling reaction with the Grignard reagent include copper halides such as cuprous chloride, cupric chloride, cuprous bromide, cupric bromide, cuprous iodide and cupric iodide. Cupric chloride is preferred from the standpoint of reactivity.

The catalyst can be used in an amount of preferably from 0.002 to 0.01 mol per mol of 5-acetoxy-(E3)-3-pentenyl methoxymethyl ether (3).

The catalyst to be used for the coupling reaction with the Grignard reagent is preferably used with an auxiliary catalyst.

Examples of the auxiliary catalyst include phosphorus compounds such as triethyl phosphite and triphenylphosphine. Triethyl phosphite is preferred from the standpoint of reactivity.

The auxiliary catalyst may be used in an amount of preferably from 0.02 to 0.05 mol per mol of 5-acetoxy-(E3)-3-pentenyl methoxymethyl ether (3).

Examples of the solvent to be used for the coupling reaction with the Grignard reagent include hydrocarbons such as toluene and hexane, and ethers such as tetrahydrofuran and diethyl ether. Tetrahydrofuran is preferred from the standpoint of a reaction rate for the formation of a Grignard reagent. The solvent can be used in an amount of preferably from 400 to 450 g per mol of 5-acetoxy-(E3)-3-pentenyl methoxymethyl ether (3).

The reaction temperature to be used for the coupling reaction with the Grignard reagent is preferably from 0 to 20° C., more preferably from 0 to 10° C. The temperature of less than 0° C. may be insufficient for the reaction to proceed smoothly, while the temperature of more than 20° C. may let the side reaction proceed.

Next, (E3)-3-alkenyl methoxymethyl ether (4) is treated with an acid to produce (E3)-3-alkenyl alcohol (5). This reaction proceeds smoothly by distilling off dimethoxymethane, a by-product, through a distillation column attached to a reactor and no EZ isomerization can be found during the reaction.

For example, (E3)-3-alkenyl methoxymethyl ether (4) is treated with an acid in a solvent to remove the methoxymethyl group.

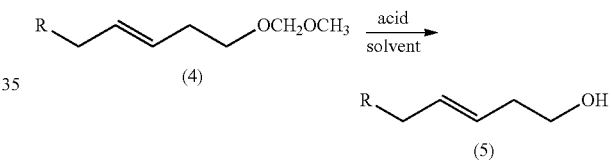

Examples of the acid include hydrogen chloride, sulfuric acid and trifluoroacetic acid. Hydrogen chloride is preferred from the standpoint of availability.

The acid used for this reaction has a concentration of preferably from 5 to 50% by weight, more preferably from 10 to 37% by weight. The concentration of less than 5% by weight may be insufficient for the reaction to proceed smoothly, while the concentration of more than 50% by weight may require severe control of temperature, pressure and the like upon use.

When, for example, a 20 wt % (20% by weight) hydrochloric acid is used as the acid, the amount of the hydrochloric acid is preferably from 300 to 400 g per mol of the (E3)-3-alkenyl methoxymethyl ether (4).

Examples of the solvent to be used for the acid treatment include various alcohols such as methanol and ethanol, ethers such as tetrahydrofuran and diethyl ether, and polar solvents such as dichloromethane. Methanol is preferred from the standpoint of reactivity. The solvent can be used in an amount of preferably from 500 to 1000 g per mol of the (E3)-3-alkenyl methoxymethyl ether (4).

The reaction temperature to be used for the acid treatment is preferably from 42 to 80° C., more preferably from 50 to 65° C. The reaction temperature of less than 42° C. may be insufficient for the reaction to proceed smoothly because dimethoxymethane cannot be distilled off. The reaction temperature of more than 80° C. may not let the reaction proceed smoothly because the solvent evaporates.

Finally, (E3)-3-alkenyl alcohol (5) reacts with an acetylating agent to produce (E)-3-alkenyl acetate (6). Examples of the acetylating agent include acetyl chloride; condensation agents such as dicyclohexylcarbodiimide; and acetic anhydride. Acetic anhydride is preferred from the standpoint of reactivity.

This reaction is conducted, for example, by reacting (E3)-3-alkenyl alcohol (5) with acetic anhydride for acetylation in a solvent in the presence of a pyridine compound or an amine compound.

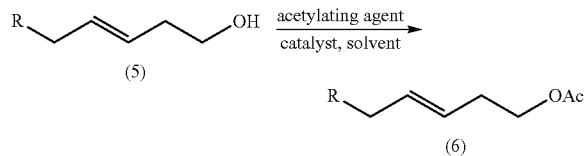

The acetylating agent can be used in an amount of preferably from 1.1 to 1.3 mol per mol of the (E3)-3-alkenyl alcohol (5). The amount of less than 1.1 mol may be insufficient for the reaction to proceed smoothly, while the amount of more than 1.3 mol may lead to wasting of the agent.

Examples of the catalyst to be used for the acetylation reaction include pyridine compounds such as pyridine and dimethylaminopyridine, and amine compounds such as triethylamine and trimethylamine. Dimethylaminopyridine is preferred from the standpoint of reactivity. The catalyst can be used in an amount of preferably from 0.002 to 0.01 mol per mol of the (E3)-3-alkenyl alcohol (5).

The acetylation reaction may proceed in a solvent-free manner, but it may be conducted in a solvent.

Examples of the solvent to be used for the acetylation reaction include hydrocarbons such as toluene and hexane, and ethers such as tetrahydrofuran and diethyl ether. Toluene is preferred from the standpoint of reactivity.

When the solvent is used, it is used in an amount of preferably 200 g or less per mol of the (E3)-3-alkenyl alcohol (5). The amount of more than 200 g may lead to wasting of the solvent and reduction in the charged amount of the reactants.

The reaction temperature to be used for the acetylation reaction is preferably from 6 to 90° C., more preferably from 6 to 70° C. The temperature of less than 6° C. may retard the reaction, while the temperature of more than 90° C. let the side reaction proceed.

EXAMPLES

The invention will hereinafter be described specifically by Examples. It should not be construed that the invention is limited to or by Examples.

Example 1

Preparation of 5-acetoxy-(E3)-3-pentenyl methoxymethyl ether

A toluene solution having 4-formyl-(E3)-3-butenyl methoxymethyl ether dissolved therein was placed in a reactor and stirred at 0 to 5° C. A sodium hydroxide solution containing 0.9% by weight sodium borohydride was added dropwise thereto at 10 to 18° C. After the dropwise addition, the resulting mixture was stirred at room temperature for 30 minutes. After stirring, the reaction mixture was extracted with toluene, and the water phase was removed, while the organic phase was washed with an aqueous solution of acetic acid.

The organic phase thus obtained was concentrated under reduced pressure by removing the solvent. The residue was distilled under reduced pressure to obtain 5-hydroxy-(E3)-3-pentenyl methoxymethyl ether (bp: 87 to 90° C./3 mmHg, 273.35 g, 1.870 mol) in a yield of 87.4%.

5-Hydroxy-(E3)-3-pentenyl methoxymethyl ether (273.36 g, 1.87 mol), toluene (238 g), acetic anhydride (47.4 g, 0.464 mol) and dimethylaminopyridine (7.42 g) were placed in the reactor and stirred at from 50 to 60° C. Acetic anhydride (191 g, 1.87 mol) was added dropwise thereto at 65 to 70° C. over 30 minutes, followed by stirring at 70° C. for one hour.

After stirring, the reaction mixture was cooled to 30° C. and the reaction was terminated with water (512 g). After the reaction mixture was separated into phases, the organic phase was washed with an aqueous solution of sodium chloride and with an aqueous solution of sodium bicarbonate, and concentrated under reduced pressure by removing the solvent. The residue was distilled under reduced pressure to obtain 5-acetoxy-(E3)-3-pentenyl methoxymethyl ether (bp: from 104 to 107° C./6 mmHg, 276.65 g, 1.47 mol) in a yield of 78.6%.

<Nuclear magnetic resonance spectrum> $^1$-NMR (300 MHz, CDCl$_3$): δ2.06 (3H, s), 2.37 (2H, dt), 2.95 (3H, s), 3.59 (2H, t), 4.53 (2H, d), 4.62 (2H, s), 5.68 (1H, dt), 5.80 (1H, dt); $^{13}$CNMR (75.6 MHz, CDCl$_3$): δ20.99, 32.70, 55.19, 65.00, 66.81, 96.40, 125.93, 132.41, 170.80

<Mass spectrum> EI-mass spectrum (70 eV): m/z 158 (M$^+$-30), 126, 98, 84, 75, 67, 54, 45, 43

<Infrared absorption spectrum> (NaCl): νmax 2937, 1740, 1231, 1031, 969

Example 2

Example 2-1

Preparation of (E3,Z8,Z11)-3,8,11-tetradecatrienyl methoxymethyl ether

Magnesium (34.3 g, 1.41 mol) and tetrahydrofuran (520 g) were placed in a reactor and stirred at 60 to 65° C. for 30 minutes. After stirring, (Z3,Z6)-3,6-nonadienyl chloride (212.41 g, 1.34 mol) was added dropwise thereto at 60 to 65° C. The resulting mixture was stirred at 70 to 75° C. for 2 hours to prepare (Z3,Z6)-3,6-nonadien-1-yl-magnesium chloride.

Copper chloride (II) (0.736 g, 0.00548 mol), triethyl phosphite (7.93 ml, 0.0462 mol) and tetrahydrofuran (82 g) were placed in the reactor. Then, 5-acetoxy-(E3)-3-pentenyl methoxymethyl ether (229.06 g, 1.217 mol) and tetrahydrofuran (82 g) were added thereto at 5 to 10° C. The resulting mixture was stirred at 0 to 5° C. for 30 minutes. After stirring, the tetrahydrofuran solution of (Z3,Z6)-3,6-nonadien-1-yl-magnesium chloride was added dropwise thereto at 0 to 5° C.

After the dropwise addition, the reaction mixture was stirred at 5 to 10° C. for 40 minutes. Then, ammonium chloride (14.6 g), an aqueous 20% by weight solution (18.2 g) of hydrogen chloride and water (362 g) were added to the reaction mixture to terminate its reaction. The water phase was removed and the organic phase was concentrated under reduced pressure by removing the tetrahydrofuran. The residue was then distilled under reduced pressure to obtain (E3,Z8,Z11)-3,8,11-tetradecatrienyl methoxymethyl ether (bp: from 152 to 154° C./5 mmHg, 270.48 g, 1.072 mol) in a yield of 88.1%.

Example 2-2

Preparation of (E3,Z8,Z11)-3,8,11-tetradecatrienyl alcohol (E3,Z8,Z11)-3,8,11-Tetradecatrienyl methoxymethyl ether (241.69 g, 0.958 mol) and methanol (618 g) were placed in a reactor equipped with a distillation column and stirred at 42 to 47° C. A 20% by weight hydrochloric acid (358 g) was added dropwise thereto at 45 to 50° C. for one hour.

After the dropwise addition, the reaction mixture was raised to 55° C. and stirred for one hour. Then, the pressure was gradually reduced to 450 mmHg to distill off a mixture of methanol and dimethoxymethane produced as a byproduct from the distillation column. The residue was stirred for 9 hours. After stirring, the reaction mixture was cooled to 25° C. and extracted with hexane (605 g). The organic phase was washed with an aqueous solution of sodium chloride and with an aqueous solution of sodium bicarbonate, and the solvent was removed under pressure. The residue was distilled under reduced pressure to obtain (E3,Z8,Z11)-3,8,11-tetradecatrienyl alcohol (bp: from 138 to 140° C./8 mmHg, 180.90 g, 0.868 mol) in a yield of 90.7%.

Example 2-3

Preparation of (E3,Z8,Z11)-3,8,11-tetradecatrienyl acetate (E3,Z8,Z11)-3,8,11-tetradecatrienyl alcohol (221.36 g, 0.851 mol), toluene (506 g), acetic anhydride (21.6 g, 0.212 mol) and dimethylaminopyridine (2.16 g) were placed in a reactor and stirred at 50 to 60° C. Acetic anhydride (86.9 g, 0.851 mol) was then added dropwise thereto at 65 to 70° C. over 30 minutes and the resulting mixture was stirred at 70° C. for one hour.

After stirring, the reaction mixture was cooled to 30° C. and the reaction was terminated with water (338 g). After the reaction mixture thus obtained was separated into phases, the organic phase was washed with an aqueous solution of sodium chloride and with an aqueous solution of sodium bicarbonate, and then concentrated under reduced pressure by removing the solvent. The residue was distilled under reduced pressure to obtain (E3,Z8,Z11)-3,8,11-tetradecatrienyl acetate (bp: from 132 to 134° C./3 mmHg, 213.10 g, 0.851 mol) in a yield of 100%.

<Nuclear magnetic resonance spectrum> $^1$H-NMR (300 MHz, CDCl$_3$): δ0.97 (3H, t), 1.42 (2H, tt), 2.02 (2H, dt), 2.04 (3H, s), 2.06 (2H, dt), 2.31 (2H, dt), 2.77 (2H, dd), 4.07 (2H, t), 5.25-5.43 (5H, m), 5.51 (2H, dt); $^{13}$C-NMR (75.6 MHz, CDCl$_3$): δ14.29, 20.55, 20.99, 25.55, 26.64, 29.33, 31.98, 32.16, 64.12, 125.41, 128.37, 129.71, 131.83, 133.19, 171.09
<Mass spectrum> EI-mass spectrum (70 eV): m/z 250 (M$^+$), 190, 175, 161, 147, 133, 122, 108, 93, 79, 67, 55, 43
[Infrared absorption spectrum] (NaCl): νmax 3010, 2931, 1743, 1238, 1035, 968

Example 3

Example 3-1

Preparation of (E3,Z8)-3,8-tetradecadienyl methoxymethyl ether

Magnesium (15.6 g, 0.64 mol) and tetrahydrofuran (60.5 g) were placed in a reactor and stirred at 60 to 65° C. for 30 minutes. After stirring, (Z3)-3-nonenyl chloride (88.70 g, 0.552 mol) was added dropwise thereto at 60 to 65° C., and stirred at 70 to 75° C. for 2 hours to prepare (Z3)-3-nonenylmagnesium chloride.

Copper chloride (II) (0.334 g, 0.00248 mol), triethyl phosphite (3.60 ml, 0.0210 mol) and tetrahydrofuran (37 g) were placed in the reactor. Then, 5-acetoxy-(E3)-3-pentenyl methoxymethyl ether (103.97 g, 0.552 mol) and tetrahydrofuran (37 g) were added thereto at 5 to 10° C., and stirred at 0 to 5° C. for 30 minutes. After stirring, the tetrahydrofuran solution of (Z3)-3-nonenylmagnesium chloride was added dropwise to the reaction mixture at 0 to 5° C.

After the dropwise addition, the reaction mixture was stirred at 5 to 10° C. for 40 minutes. Then, ammonium chloride (6.6 g), a 20% by weight hydrochloric acid (8.3 g) and water (164 g) were added to the reaction mixture to terminate the reaction. The water phase was removed, while the organic phase was concentrated under reduced pressure by removing tetrahydrofuran. The residue was distilled under reduced pressure to obtain (E3,Z8)-3,8-tetradecadienyl methoxymethyl ether (bp: from 152 to 154° C./5 mmHg, 270.48 g, 1.072 mol) in a yield of 88.1%.

Example 3-2

Preparation of (E3,Z8)-3,8-tetradecadienyl alcohol (E3,Z8)-3,8-tetradecadienyl methoxymethyl ether (115.22 g, 0.4529 mol) and methanol (292 g) were placed in a reactor equipped with a distillation column and stirred at 42 to 47° C. A 20% by weight hydrochloric acid (169 g) was then added dropwise thereto at 45 to 50° C. for one hour.

After the dropwise addition, the reaction mixture was raised to 55° C. and stirred for one hour. A mixture of dimethoxymethane and methanol produced as byproducts from the distillation column was distilled off by gradually reducing the pressure to 450 mmHg and the residue was stirred for 9 hours. After stirring, the reaction mixture was cooled to 25° C. and extracted with hexane (286 g). The organic phase was washed with an aqueous solution of sodium chloride and with an aqueous solution of sodium bicarbonate. The solvent was removed under reduced pressure. The residue was then distilled under reduced pressure to obtain (E3,Z8)-3,8-tetradecadienyl alcohol (bp: 128 to 133° C./6 mmHg, 78.12 g, 0.3714 mol) in a yield of 82.0%.

Example 3-3

Preparation of (E3,Z8)-3,8-tetradecadienyl acetate (E3,Z8)-3,8-Tetradecadienyl alcohol (74.59 g, 0.3546 mol), toluene (211 g), acetic anhydride (9.0 g, 0.088 mol) and dimethylaminopyridine (0.90 g) were placed in a reactor and stirred at 50 to 60° C. Acetic anhydride (36.2 g, 0.355 mol) was added dropwise thereto at 65 to 70° C. over 30 minutes and stirred at 70° C. for one hour.

After stirring, the reaction mixture was cooled to 30° C. and the reaction was terminated with water (141 g). The reaction mixture thus obtained was separated into phases. The organic phase was washed with an aqueous solution of sodium chloride and with an aqueous solution of sodium bicarbonate, and then concentrated under reduced pressure by removing the solvent. The residue was distilled off under reduced pressure to obtain (E3,Z8)-3,8-tetradecadienyl acetate (bp: from 153 to 159° C./6 mmHg, 86.80 g, 0.344 mol) in a yield of 97%.

<Nuclear magnetic resonance spectrum> $^1$H-NMR (300 MHz, CDCl$_3$): δ0.89 (3H, t), 1.29 (8H, m), 1.42 (2H, dt), 2.02 (4H, m), 2.03 (3H, s), 2.31 (2H, dt), 4.07 (2H, t), 5.36 (3H, m), 5.52 (1H, dt); $^{13}$C-NMR (75.6 MHz, CDCl$_3$): δ14.08, 20.98, 22.59, 26.64, 27.22, 29.45, 29.45, 31.54, 31.98, 32.18, 33.09, 64.13, 125.31, 129.38, 130.31, 133.29, 171.09

<Mass spectrum> EI-mass spectrum (70 eV): m/z 192 (M$^+$-60), 163, 149, 135, 121, 107, 95, 80, 67, 55, 43

<Infrared absorption spectrum> (NaCl): νmax 3004, 2925, 1743, 1238, 1035, 968

The invention claimed is:

1. A method for preparing an (3E)-3-alkenyl acetate comprising at least the steps of:

reacting 4-formyl-(3E)-3-butenyl methoxymethyl ether with a reductant to obtain 5-hydroxy-(3E)-3-pentenyl methoxymethyl ether;

reacting the 5-hydroxy-(3E)-3-pentenyl methoxymethyl ether with an acetylating agent to obtain 5-acetoxy-(3E)-3-pentenyl methoxymethyl ether;

subjecting the 5-acetoxy-(3E)-3-pentenyl methoxymethyl ether to a coupling reaction at a temperature of from 0 to 20° C. with a Grignard reagent, wherein the Grignard reagent is (Z3,Z6)-3,6-nonadienylmagnesium halide or (Z3)-3-nonenylmagnesium halide, so that the 5-acetoxy group is replaced by either (Z3,Z6)-3,6-nonadienyl or (Z3)-3-nonenyl to obtain (3E)-3-alkenyl methoxymethyl ether;

treating the (3E)-3-alkenyl methoxymethyl ether with an acid to obtain (3E)-3-alkenyl alcohol; and reacting the (3E)-3-alkenyl alcohol with an acetylating agent to obtain the (3E)-3-alkenyl acetate, wherein the reductant is sodium borohydride and the (3E)-3-alkenyl acetate is (3E,Z8,Z11)-3,8,11-tetradecatrienyl acetate or (3E,ZS)-3,8-tetradecadienyl —acetate.

* * * * *